United States Patent [19]

Craig, Jr. et al.

[11] Patent Number: 4,869,253

[45] Date of Patent: Sep. 26, 1989

[54] METHOD AND APPARATUS FOR INDICATING PERFUSION AND OXYGEN SATURATION TRENDS IN OXIMETRY

[75] Inventors: Kenneth C. Craig, Jr., Bellevue; Karl F. Gauglitz, Kirkland; G. Michael Losh, Mercer Island; Lee R. Mason, Issaquah; Richard C. Nova, Kirkland; James W. Taylor, Bothell; Stephen J. Prosser, Lynnwood, all of Wash.

[73] Assignee: Physio-Control Corporation, Redmond, Wash.

[21] Appl. No.: 897,662

[22] Filed: Aug. 18, 1986

[51] Int. Cl.$^4$ .............................................. A61B 5/00
[52] U.S. Cl. .................................. 128/633; 128/664; 128/665; 340/753; 340/573
[58] Field of Search ............... 128/633, 634, 664, 665, 128/666; 340/573, 753

[56] References Cited

U.S. PATENT DOCUMENTS

| | | |
|---|---|---|
| 2,706,927 | 4/1955 | Wood . |
| 3,704,706 | 12/1972 | Hertzfeld et al. . |
| 3,847,483 | 11/1974 | Shaw et al. . |
| 3,894,533 | 7/1975 | Cannon .................... 128/671 |
| 3,998,550 | 12/1976 | Konishi et al. . |
| 4,013,067 | 3/1977 | Kresse et al. .................... 128/666 |
| 4,086,915 | 5/1978 | Kofsky et al. . |
| 4,109,634 | 8/1978 | Bond et al. . |
| 4,114,604 | 9/1978 | Shaw et al. . |
| 4,167,331 | 9/1979 | Nielsen . |
| 4,222,389 | 9/1980 | Rubens . |
| 4,266,554 | 5/1981 | Hamaguri . |
| 4,407,290 | 10/1983 | Wilber . |
| 4,450,843 | 5/1984 | Barney et al. .................... 128/690 |
| 4,453,218 | 6/1984 | Sperinde et al. . |
| 4,461,301 | 7/1984 | Ochs .................... 128/630 |
| 4,463,762 | 8/1984 | Rubens . |
| 4,653,498 | 3/1987 | New et al. .................... 128/666 |
| 4,689,615 | 8/1987 | Del Rosso .................... 340/753 |
| 4,697,450 | 10/1987 | Bachman et al. .................... 128/635 |
| 4,765,340 | 8/1988 | Sakai et al. .................... 128/633 |

FOREIGN PATENT DOCUMENTS 83304938.0 8/1983 .
83304939.8 8/1983 European Pat. Off. .

OTHER PUBLICATIONS

EPA, 0,194,105, A2, Nichols et al., Sep. 9, 1986.
Waït et al., Intro. to Operational Amplifier Theory, McGraw-Hill, NY, 1975, pp. 50-51.

Primary Examiner—Lee S. Cohen
Assistant Examiner—John C. Hanley
Attorney, Agent, or Firm—Christensen, O'Connor, Johnson & Kindness

[57] ABSTRACT

The present invention discloses a method and apparatus for indicating perfusion and oxygen saturation trends in oximetry. In transmittance and reflectance oximetry, LEDs (40, 42) are typically employed to expose tissue to light at two different wavelengths. The light transmitted through, or reflected by, the tissue is received by a detector (38) where signals proportional to the intensity of light are produced. These signals are then processed by oximeter circuitry (14, 16) to determine oxygen saturation, pulse rate, and perfusion. Displays (20) are provided including a display (132, 134) of the change in the oxygen saturation during a specified interval. This display may include first (132) and second (134) trend indication displays that indicate when the oxygen saturation has either been increasing or decreasing at a rate in excess of some predetermined level. Preferably, these displays are triangular, upwardly and downwardly directed light-emitting diodes. A digital display (138) of the change in oxygen saturation may also be provided. A second type of display included provides pulse and perfusion information, with the perfusion being displayed as a logarithmic function of the actual perfusion. This display comprises an aligned array of light-emitting diodes (136) with the number of LED's lit imaging the plethysmigraphic waveform, peak to peak scaling is employed which is indicative of signal level and perfusion.

4 Claims, 9 Drawing Sheets

METHOD AND APPARATUS FOR INDICATING PERFUSION AND OXYGEN SATURATION TRENDS IN OXIMETRY

BACKGROUND OF THE INVENTION

This invention relates to oximetry and, more particularly, to signal-processing techniques employed in oximetry.

The arterial oxygen saturation and pulse rate of an individual may be of interest for a variety of reasons. For example, in the operating room up-to-date information regarding oxygen saturation can be used to signal changing physiological factors, the malfunction of anaesthesia equipment, or physician error. Similarly, in the intensive care unit, oxygen saturation information can be used to confirm the provision of proper patient ventilation and allow the patient to be withdrawn from a ventilator at an optimal rate.

In many applications, particularly including the operating room and intensive care unit, continual information regarding pulse rate and oxygen saturation is important if the presence of harmful physiological conditions is to be detected before a substantial risk to the patient is presented. A noninvasive technique is also desirable in many applications, for example, when a home health care nurse is performing a routine checkup, because it increases both operator convenience and patient comfort. Pulse transmittance oximetry is addressed to these problems and provides noninvasive, continual information about pulse rate and oxygen saturation. The information produced, however, is only useful when the operator can depend on its accuracy. The method and apparatus of the present invention are, therefore, directed to the improved accuracy of such information without undue cost.

As will be discussed in greater detail below, pulse transmittance oximetry basically involves measurement of the effect arterial blood in tissue has on the intensity of light passing therethrough. More particularly, the volume of blood in the tissue is a function of the arterial pulse, with a greater volume present at systole and a lesser volume present at diastole. Because blood absorbs some of the light passing through the tissue, the intensity of the light emerging from the tissue is inversely proportional to the volume of blood in the tissue. Thus, the emergent light intensity will vary with the arterial pulse and can be used to indicate a patient's pulse rate. In addition, the absorption coefficient of oxyhemoglobin (hemoglobin combined with oxygen, $HbO_2$) is different from that of deoxygenated hemoglobin (Hb) for most wavelengths of light. For that reason, differences in the amount of light absorbed by the blood at two different wavelengths can be used to indicate the hemoglobin oxygen saturation, % $SaO_2$ (OS), which equals $([HbO_2]/([Hb]+[HbO_2]))\times 100\%$. Thus, measurement of the amount of light transmitted through, for example, a finger can be used to determine both the patient's pulse rate and hemoglobin oxygen saturation.

As will be appreciated, the intensity of light transmitted through a finger is a function of the absorption coefficient of both "fixed" components, such as bone, tissue, skin, and hair, as well as "variable" components, such as the volume of blood in the tissue. The intensity of light transmitted through the tissue, when expressed as a function of time, is often said to include a baseline component, which varies slowly with time and represents the effect of the fixed components on the light, as well as a periodic pulsatile component, which varies more rapidly with time and represents the effect that changing tissue blood volume has on the light. Because the attenuation produced by the fixed tissue components does not contain information about pulse rate and arterial oxygen saturation, the pulsatile signal is of primary interest. In that regard, many of the prior art transmittance oximetry techniques eliminate the so-called "DC" baseline component from the signal analyzed.

For example, in U.S. Pat. No. 2,706,927 (Wood) measurements of light absorption at two wavelengths are taken under a "bloodless" condition and a "normal" condition. In the bloodless condition, as much blood as possible is squeezed from the tissue being analyzed. Then, light at both wavelengths is transmitted through the tissue and absorption measurements made. These measurements indicate the effect that all nonblood tissue components have on the light. When normal blood flow has been restored to the tissue, a second set of measurements is made that indicates the influence of both the blood and nonblood components. The difference in light absorption between the two conditions is then used to determine the average oxygen saturation of the tissue, including the effects of both arterial and venous blood. As will be readily apparent, this process basically eliminates the DC, nonblood component from the signal that the oxygen saturation is extracted from.

For a number of reasons, however, the Wood method fails to provide the necessary accuracy. For example, a true bloodless condition is not practical to obtain. In addition, efforts to obtain a bloodless condition, such as by squeezing the tissue, may result in a different light transmission path for the two conditions. In addition to problems with accuracy, the Wood approach is both inconvenient and time consuming.

A more refined approach to pulse transmittance oximetry is disclosed in U.S. Pat. No. 4,167,331 (Nielson). The disclosed oximeter is based upon the principle that the absorption of light by a material is directly proportional to the logarithm of the light intensity after having been attenuated by the absorber, as derived from the Beer-Lambert law. The oximeter employs light-emitting diodes (LEDs) to produce light at red and infrared wavelengths for transmission through tissue. A photosensitive device responds to the light produced by the LEDs and attenuated by the tissue, producing an output current. That output current is amplified by a logarithmic amplifier to produce a signal having AC and DC components and containing information about the intensity of light transmitted at both wavelengths. Sample-and-hold circuits demodulate the red and infrared wavelength signals. The DC components of each signal are then blocked by a series bandpass amplifier and capacitors, eliminating the effect of the fixed absorptive components from the signal. The resultant AC signal components are unaffected by fixed absorption components, such as hair, bone, tissue, skin. An average value of each AC signal is then produced. The ratio of the two averages is then used to determine the oxygen saturation from empirically determined values associated with the ratio. The AC components are also used to determine the pulse rate.

Another reference addressed to pulse transmittance oximetry is U.S. Pat. No. 4,407,290 (Wilber). In that reference, light pulses produced by LEDs at two different wavelengths are applied to, for example, an earlobe.

A sensor responds to the light transmitted through the earlobe, producing a signal for each wavelength having a DC and AC component resulting from the presence of constant and pulsatile absorptive components in the earlobe. A normalization circuit employs feedback to scale both signals so that the DC nonpulsatile components of each are equal and the offset voltages removed. Decoders separate the two signals, so controlled, into channels A and B where the DC component from each is removed. The remaining AC components of the signals are amplified and combined at a multiplexer prior to analog-to-digital (A/D) conversion. Oxygen saturation is determined by a digital processor in accordance with the following relationship:

$$OS = \frac{X_1 R(\lambda_1) + X_2 R(\lambda_2)}{X_3 R(\lambda_1) + X_4 R(\lambda_2)}$$

wherein empirically derived data for the constants $X_1$, $X_2$, $X_3$ and $X_4$ is stored in the processor.

European patent application No. 83304939.8 (New, Jr. et al.) discloses an additional pulse transmittance oximeter. Two LEDs expose a body member, for example, a finger, to light having red and infrared wavelengths, with each LED having a one-in-four duty cycle. A detector produces a signal in response that is then split into two channels. The one-in-four duty cycle allows negatively amplified noise signals to be integrated with positively amplified signals including the detector response ane noise, thereby eliminating the effect of noise on the signal produced. The resultant signals include a substantially constant DC component and a pulsatile AC component. To improve the accuracy of a subsequent analog-to-digital (A/D) conversion, a fixed DC value is subtracted from the signal prior to the conversion. This level is then added back in by a microprocessor after the conversion. Logarithmic analysis is avoided by the microprocessor in the following manner. For each wavelength of light transmitted through the finger, a quotient of the pulsatile component over the constant component is determined. The ratio of the two quotients is then determined and fitted to a curve of independently derived oxygen saturations. To compensate for the different transmission characteristics of different patients' fingers, an adjustable drive source for the LEDs is provided. In addition, an apparatus for automatically calibrating the device is disclosed.

European patent application No. 83304938.0 (New, Jr. et al.) discloses a pulse oximeter monitor having a variety of displays. For example, digital displays of oxygen saturation and pulse rate are provided. In addition, an indicator having a plurality of LEDs is provided wherein the number of LEDs strobed is proportional to the magnitude of the pulse and the strobe rate is proportional to the pulse. An audible tone signal is provided having a pitch that is proportional to the oxygen saturation and a repetition rate that is proportional to pulse. Adjustable alarm limits are provided for high and low pulse rates as well as oxygen saturation levels. Separate selector switches indicate the alarm limit to be adjusted and a limit knob is used to set the level. Default limits are initially assigned to these values and in the event an alarm limit is exceeded, a constant-pitch, continuous audible tone is produced. Upon start-up, a sync status light indicates that a pulse has not been established.

While the displays disclosed by New, Jr. et al. provide information to the oximeter operator, additional information may be advantageously extracted by the oximeter. It is the display of certain types of this additional information to which the present invention is directed.

SUMMARY OF THE INVENTION

According to the present invention, an apparatus is disclosed for processing signals containing information about the oxygen saturation of arteria blood flowing in tissue. The apparatus includes a processor that determines the oxygen saturation of the arterial blood flowing in the tissue from the signals and a display that produces an output indicative of the change in the oxygen saturation during a specified interval.

In accordance with a particular aspect of the invention, the display means includes first and second trend indication displays. The first trend indication display produces an output when the oxygen saturation has increased by a first predetermined amount during the specified interval. Similarly, the second trend indication display produces an output when the oxygen saturation has decreased by a second predetermined amount during the specified interval. The first predetermined amount, second predetermined amount, and specified interval can be selectively controlled. With, for example, the first and second predetermined amounts being set at a three percent change in oxygen saturation and the specified interval being set at two minutes. The first trend indication display may be extinguished when the oxygen saturation fails to increase by a third predetermined amount over a second specified interval (e.g., 2.5% over 2 minutes), and the second trend indication display extinguished when the oxygen saturation fails to decrease by a fourth predetermined amount over the second predetermined interval (e.g., 2.5% over 2 minutes). In one embodiment, the first and second trend indication displays are upwardy and downwardly directed triangular light-emitting diodes. As an alternative to, or for use in conjunction with, the first and second trend indication displays, the display may provide a numeric representation of the change in oxygen saturation.

In accordance with another aspect of the invention, an apparatus is disclosed for processing signals containing information about the pulse rate and perfusion of arterial blood flowing therein. A detection means produces signals that are proportional to the intensity of light received from the tissue in response to the illumination. Processing means then determine the oxygen saturation, pulse rate, and perfusion of the arterial blood from the signals produced by the detection means. An output indicative of the pulse rate and perfusion is produced by a display means, with the perfusion being displayed as a logarithmic function of the perfusion determined by the processing means.

In accordance with further aspects of the invention, the display means may automatically scale the perfusion displayed to produce a full-scale display at peak perfusion when the signal level exceeds a predetermined level. The display means may conveniently comprise an aligned array of light-emitting diodes, with the number of light-emitting diodes lit at any one time imaging pleth. Waveform, peak to peak scaling is employed which is indicative of signal level and perfusion.

BRIEF DESCRIPTION OF THE DRAWINGS

The invention can best be understood by reference to the following portion of the specification, taken in conjunction with the accompanying drawings in which.

DETAILED DESCRIPTION

Figure 1:
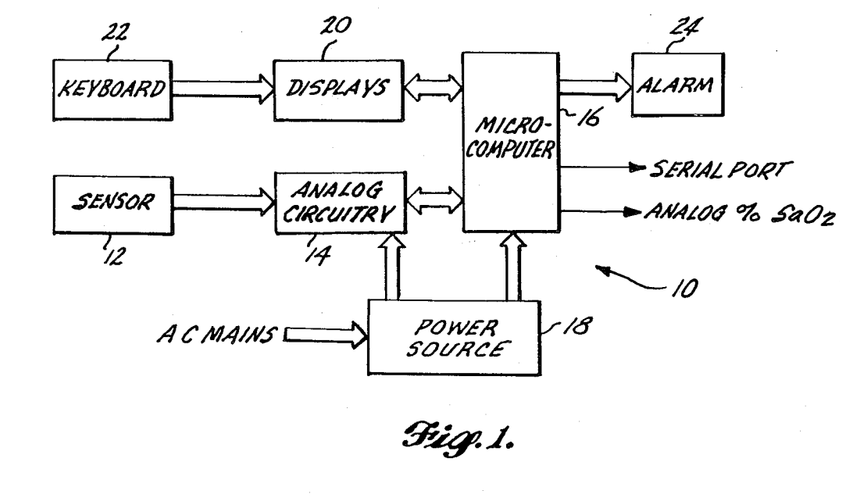
FIG. 1 is block diagram of an oximeter including a sensor, input/output (I/O) circuit, microcomputer, alarm, displays, power supply, and keyboard.

Referring to the overall system block diagram shown in FIG. 1, a pulse transmittance oximeter 10 employing this invention includes a sensor 12, input/output (I/O) circuit 14, microcomputer 16, power source 18, display 20, keyboard 22 and alarm 24. Before discussing these elements in detail, however, an outline of the theoretical basis of pulse transmittance oximetry as practiced by the oximeter of FIG. 1 is provided.

An understanding of the relevent theory begins with a discussion of the Beer-Lambert law. This law governs the absorption of optical radiation by homogeneous absorbing media and can best be understood with reference to FIGS. 2 and 3 in the following manner.

Figure 2:
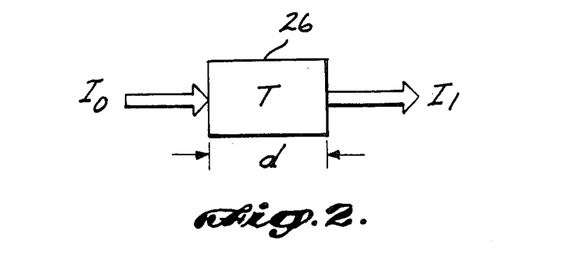
FIG. 2 is a block diagram illustrating the transmission of light through an absorptive medium.
Figure 3:
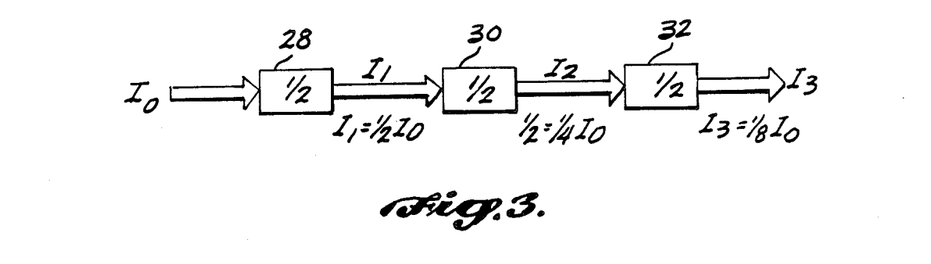
FIG. 3 is a block diagram illustrating the transmission of light through the absorptive medium of FIG. 2, wherein the medium is broken up into elemental components.

As shown in FIG. 2, incident light having an intensity $I_0$ impinges upon an absorptive medium 26. Medium 26 has a characteristic absorbance factor A that indicates the attenuating affect medium 26 has on the incident light. Simlarly, a transmission factor T for the medium is defined as the reciprocal of the absorbance factor, $I/A$. The intensiy of the light $I_1$ emerging from medium 26 is less than $I_0$ and can be expressed functionally as the product $TI_0$. With medium 26 divided into a number of identical components, each of unit thickness (in the direction of light transmission) and the same transmission factor T, the effect of medium 26 on the incident light $I_0$ is as shown in FIG. 3.

There, medium 26 is illustrated as consisting of three components 28, 30, and 32. As will be appreicated, the intensity $I_1$ of the light emerging from component 28 is equal to the incident light intensity $I_0$ multiplied by the transmission factor T. Component 30 has a similar effect on light passing therethrough. Thus, because the light incident upon component 30 is equal to the product $TI_0$, the emergent light intensity $I_2$ is equal to the product $TI_1$ or $T^2I_0$. Component 32 has the same effect on light and, as shown in FIG. 3, the intensity of the emergent light $I_3$ for the entire medium 26 so modeled is equal to the product $TI_2$ or $T^3I_0$. If the thickness d of medium 26 is n unit lengths, it can be modeled as including n identical components of unit thickness. It will then be appreciated that the intensity of light emerging from medium 26 can be designated $I_n$ and the product is equal to $T^nI_0$. Expressed as a function of the absorbance constant A, $I_n$ can also be written as the product $(1/A^n)I_0$.

From the preceding discussion, it will be readily appreicated that the absorptive effect of medium 26 on the intensity of the incident light $I_0$ is one of exponential decay. Because A may be an inconvenient base to work with, $I_n$ can be rewritten as a function of a more convenient base, b, by recognizing that $A^n$ is equal to $b^{\alpha n}$, where $\alpha$ is the absorbance of medium 26 per unit length. The term $\alpha$ is frequently referred to as the relative extinction coefficient and is equal to $\log_b A$.

Figure 4:
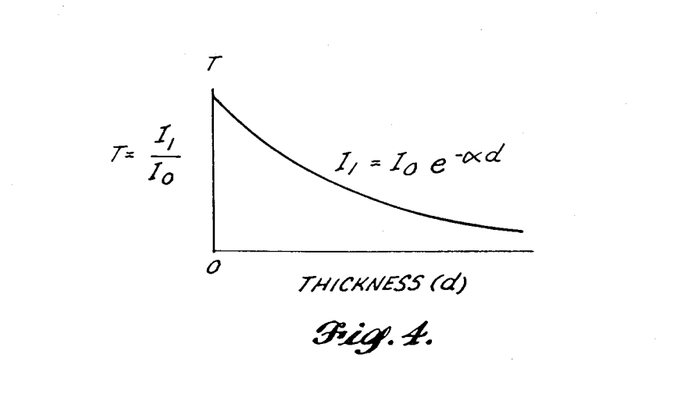
FIG. 4 is a graphical comparison of the incident light intensity to the emergent light intensity as modeled in FIG. 2.

Given the preceding discussion, it will be appreciated that the intensity of the light $I_n$ emerging from medium 26 can be expressed in base 10 (where $\alpha=\alpha_1$) as $I_010^{-\alpha_1 n}$, or in base e (where $\alpha=\alpha_2$) as $I_0 e^{-\alpha_2 n}$. The effect that the thickness of medium 26 has on the emergent light intensity $I_n$ is graphically depicted in FIG. 4. If the light incident upon medium 26 is established as having unit intensity, FIG. 4 also represents the transmission factor T of the entire medium as a function of thickness.

The discussion above can be applied generally to the medium 26 shown in FIG. 2 to produce:

$$I_1 = I_0 e^{-\alpha d} \qquad (1)$$

where $I_1$ is the emergent light intensity, $I_0$ is the incident light intensity, $\alpha$ is the absorbance coefficient of the medium per unit length, d is the thickness of the medium in unit lengths, and the exponential nature of the relationship has arbitrarily been expressed in terms of base e. Equation (1) is commonly referred to as the Beer-Lambert law of exponential light decay through a homogeneous absorbing medium.

Figure 5:
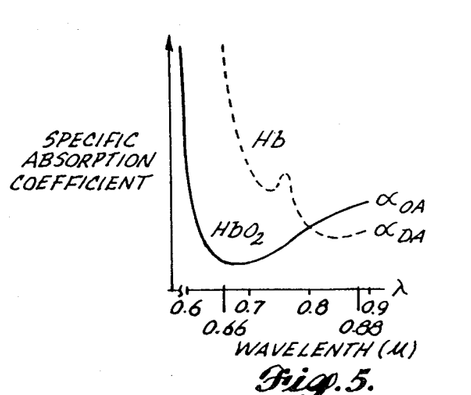
FIG. 5 is a graphical comparison of the specific absorption coefficients for oxygenated hemoglobin and deoxygenated hemoglobin as a function of the wavelength of light transmitted therethrough.

With this basic understanding of the Beer-Lambert law, a discussion of its application to the problems of pulse rate and hemoglobin oxygen saturation measurement is now presented. As shown in FIG. 5, the absorption coefficients for oxygenated and deoxygenated hemoglobin are different at every wavelength, except an isobestic wavelength. Thus, it will be appreciated that if a person's finger is exposed to incident light and the emergent light intensity measured, the difference in intensity between the two, which is the amount of light absorbed, contains information relating to the oxygenated hemoglobin content of the blood in the finger. The manner in which this information is extracted from the Beer-Lambert law is discussed below. In addition, it will be appreciated that the volume of blood contained within an individual's finger varies with the individual's pulse. Thus, the thickness of the finger also varies slightly with each pulse, creating a changing path length for light transmitted through the finger. Because a longer lightpath allows additional light to be absorbed, time-dependent information relating to the difference between the incident and emergent light intensities can be used to determine the individual's pulse. The manner in which this information is extracted from the Beer-Lambert law is also discussed below.

As noted in the preceding paragraph, information about the incident and emergent intensities of light transmitted through a finger can be used to determine oxygen saturation and pulse rate. The theoretical basis for extracting the required information, however, is complicated by several problems. For example, the precise intensity of the incident light applied to the finger is not easily determined. Thus, it may be necessary to extract the required information independently of the intensity of the incident light. Further, because the changing volume of blood in the finger and, hence, thickness of the lightpath therethrough, are not exclusively dependent upon the individual's pulse, it is desirable to eliminate the changing path length as a variable from the computations.

Figure 6:
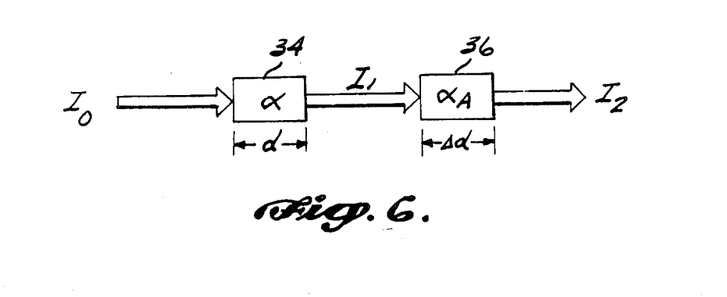
FIG. 6 is a block diagram illustrating the transmission of light through a block model of the components of a finger.

The manner in which the Beer-Lambert law is refined to eliminate the incident intensity and path length as variables is as follows. With reference to FIG. 6, a human finger is modeled by two components 34 and 36, in a manner similar to that shown in FIG. 3. Baseline component 34 models the unchanging absorptive elements of the finger. This component includes, for example, bone, tissue, skin, hair, and baseline venous and arterial blood and has a thickness designated d and an absorbance $\alpha$.

Pulsatile component 36 represents the changing absorptive portion of the finger, the arterial blood volume. As shown, the thickness of this component is designated $\Delta d$, representing the variable nature of the thickness, and the absorbance of this arterial blood component is designated $\alpha_A$ representing the arterial blood absorbance.

As will be appreciated from the earlier analysis with respect to FIG. 3, the light $I_1$ emerging from component 34 can be written as a function of the incident light intensity $I_0$ as follows:

$$I_1 = I_0 e^{-\alpha d} \quad (2)$$

Likewise, the intensity of light $I_2$ emerging from component 36 is a function of its incident light intensity $I_1$, and:

$$I_2 = I_1 e^{-\alpha_A \Delta d} \quad (3)$$

Substitution of the expression for $I_1$ developed in equation (2) for that used in equation (3), where simplified results in the following expression for the intensity $I_2$ of light emerging from the finger as a function of the intensity of light $I_0$ incident upon the finger:

$$I_2 = I_0 e^{-[\alpha d + \alpha_A \Delta d]} \quad (4)$$

Because our interest lies in the effect on the light produced by the arterial blood volume, the relationship between $I_2$ and $I_1$ is of particular interest. Defining the change in transmission produced by the arterial component 36 as $T_{\Delta A}$, we have:

$$T_{\Delta A} = I_2 / I_1 \quad (5)$$

Substituting the expressions for $I_1$ and $I_2$ obtaind in equations (2) and (3), respectively, equation (5) becomes:

$$T_{\Delta A} = \frac{I_0 e^{-[\alpha d + \alpha_A \Delta d]}}{I_0 e^{-\alpha d}} \quad (6)$$

It will be appreciated that the $I_0$ term can be cancelled from both the numerator and denominator of equation (6), thereby eliminating the input light intensity as a variable in the equation. With equation (6) fully simplified, the change in arterial transmission can be expressed as:

$$T_{\Delta A} = e^{-\alpha_A \Delta d} \quad (7)$$

A device employing this principle of operation is effectively self-calibrating, being independent of the incident light intensity $I_0$.

At this point, a consideration of equation (7) reveals that the changing thickness of the finger, $\Delta d$, produced by the changing arterial blood volume still remains as a variable. The $\Delta d$ variable is eliminated in the following manner. For convenience of expression, the logarithms of the terms in equation (7) are produced with respect to the same base originally employed in equation (1). Thus, equation (7) becomes:

$$\ln T_{\Delta A} = \ln(e^{-\alpha_A \Delta d}) = -\alpha_A \Delta d \quad (8)$$

A preferred technique for eliminating the $\Delta d$ variable utilizes information drawn from the change in arterial transmission experienced at two wavelengths.

The particular wavelengths selected are determined in part by consideration of a more complete expression of the arterial absorbance $\alpha_A$:

$$\alpha_A = (\alpha_{OA})(OS) - (\alpha_{DA})(1-OS) \quad (9)$$

where $\alpha_{OA}$ is the oxygenated arterial absorbance, $\alpha_{DA}$ is the deoxygenated arterial absorbance, and OS is the hemoglobin oxygen saturation of the arterial blood volume. As will be appreciated from FIG. 5, $\alpha_{OA}$ and $\alpha_{DA}$ are substantially unequal at all light wavelengths in the red and near-infrared wavelength regions except for an isobestic wavelength occurring at approximately 805 nanometers. With an arterial oxygen saturation OS of approximately 90 percent, it will be appreciated from equation (9) that the arterial absorbance $\alpha_A$ is 90 percent attributable to the oxygenated arterial absorbance $\alpha_{OA}$ and 10 percent attributable to the deoxygenated arterial absorbance $\alpha_{DA}$. At the isobestic wavelength, the relative contribution of these two coefficients to the arterial absorbance $\alpha_A$ is of minimal significance in that both $\alpha_{OA}$ and $\alpha_{DA}$ are equal. Thus, a wavelength roughly approximating the isobestic wavelength of the curves illustrated in FIG. 5 is a convenient one for use in eliminating the change in finger thickness $\Delta d$ attributable to arterial blood flow.

A second wavelength is selected at a distance from the approximately isobestic wavelength that is sufficient to allow the two signals to be easily distinguished. In addition, the relative difference of the oxygenated and deoxygenated arterial absorbances at this wavelength is more pronounced. In light of the foregoing considerations, it is generally preferred that the two wavelengths selected fall within the red and infrared regions of the electromagnetic spectrum.

The foregoing information, when combined with equation (8) is used to produce the following ratio:

$$\frac{\ln T_{\Delta AR}}{\ln T_{\Delta AIR}} = \frac{-\alpha_A \Delta d @ \lambda_R}{-\alpha_A \Delta d @ \lambda_{IR}} \qquad (10)$$

where $T_{\Delta AR}$ equals the change in arterial transmission of light at the red wavelength $\lambda_R$ and $T_{\Delta AIR}$ is the change in arterial transmission at the infrared wavelength $\lambda_{IR}$. It will be appreciated that if two sources are positioned at substantially the same location on the finger, the length of the lightpath through the finger is substantially the same for the light emitted by each. Thus, the change in the lightpath resulting from arterial blood flow, $\Delta d$, is substantially the same for both the red and infrared wavelength sources. For that reason, the $\Delta d$ term in the numerator and denominator of the right-hand side of equation (10) cancel, producing:

$$\frac{\ln T_{\Delta AR}}{\ln T_{\Delta AIR}} = \frac{\alpha_A @ \lambda_R}{\alpha_A @ \lambda_{IR}} \qquad (11)$$

As will be appreciated, equation (11) is independent of both the incident light intensity $I_0$ and the change in finger thickness $\Delta d$ attributable to arterial blood flow. The foregoing derivations form the theoretical basis of pulse oximetry measurement. Because of the complexity of the physiological process, however, the ratio indicated in equation (11) does not directly provide an accurate measurement of oxygen saturation. The correlation between the ratio of equation (11) and actual arterial blood gas measurements is, therefore, relied on to produce an indication of the oxygen saturation. Thus, if the ratio of the arterial absorbance at the red and infrared wavelengths can be determined, the oxygen saturation of the arterial blood flow can be extracted from independently derived, empirical calibration curves in a manner independent of $I_0$ and $\Delta d$.

For simplicity, a measured ratio $R_{OS}$ is defined from equation (11) as:

$$\text{Ratio} = R_{OS} = \frac{\alpha_A @ \lambda_R}{\alpha_A @ \lambda_{IR}} \qquad (12)$$

Figure 7:
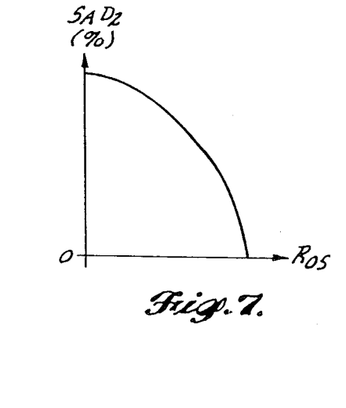
FIG. 7 is a graphical comparison of empirically derived oxygen saturation measurements related to a measurable value determined by the oximeter.

It is this measured value for $R_{OS}$ that is plotted on the x-axis of independently derived oxygen saturation curves, as shown in FIG. 7 and discussed in greater detail below, with the hemoglobin oxygen saturation being referenced on the y-axis.

Figure 8:
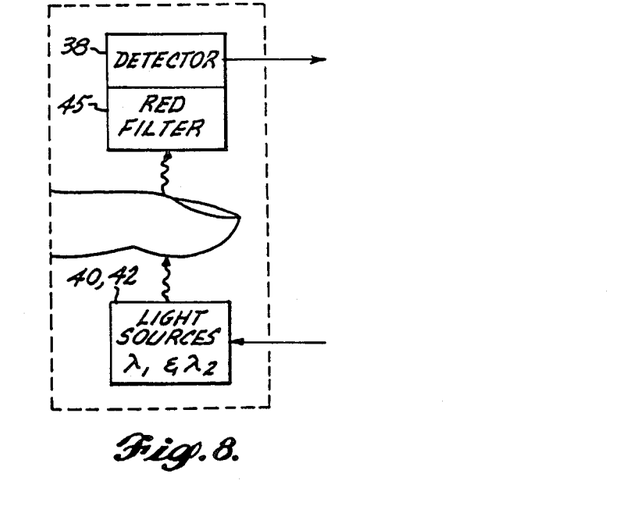
FIG. 8 is a schematic illustration of the transmission of light at two wavelengths through a finger in accordance with the invention.
Figure 9:
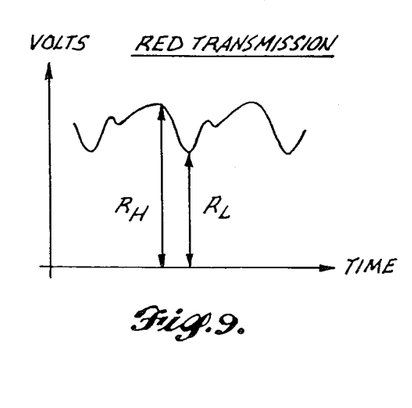
FIG. 9 is a graphical plot as a function of time of the transmittance of light at the red wavelength through the finger.

Measurement of the arterial absorbances at both wavelengths is performed in the following manner. As shown in FIG. 8, a detector 38 placed on the side of a finger opposite red and infrared wavelength light sources 40 and 42 receives light at both wavelengths transmitted through the finger. As shown in FIG. 9, the received red wavelength light intensity, plotted as a function of time, varies with each pulse, and has high and low values $R_H$ and $R_L$, respectively. $R_L$ occurs substantially at systole, when arterial blood volume is at its greatest; while $R_H$ occurs substantially at diastole, when the arterial blood volume is lowest. From the earlier discussion of the exponential light decay through homogeneous media, it will be appreciated that:

$$R_L = I_0 e^{-[\alpha d + \alpha_A \Delta d]} @ \lambda_R \qquad (13)$$

Similarly:

$$R_H = I_0 e^{-\alpha d} @ \lambda_R \qquad (14)$$

Taking the ratio of equations (13) and (14) and simplifying, we have:

$$\frac{R_L}{R_H} = I_0 \frac{e^{-[\alpha d + \alpha_A \Delta d]}}{I_0 e^{-\alpha d}} @ \lambda_R = e^{-\alpha_A \Delta d} @ \lambda_R \qquad (15)$$

Taking the logarithm of both sides of equation (15) produces:

$$\ln(R_L/R_H) = \ln(e^{-\alpha_A \Delta d}) @ \lambda_R = -\alpha_A \Delta d @ \lambda_R \qquad (16)$$

As will be readily appreciated, similar expression can be produced for the signals representative of the infrared wavelength light received by detector 38. Thus, the minimum light intensity passing through the finger at the infrared wavelength can be written:

$$IR_L = I_0 e^{-[\alpha d + \alpha_A \Delta d]} @ \lambda_{IR} \qquad (17)$$

Similarly, the maximum light intensity emerging from the finger at the infrared wavelength can be expressed as:

$$IR_H = I_0 e^{-\alpha d} @ \lambda_{IR} \qquad (18)$$

The ratio of the terms in equations (17) and (18) can be expressed as:

$$\frac{IR_L}{IR_H} = I_0 \frac{e^{-[\alpha d + \alpha_A \Delta d]}}{I_0 e^{-\alpha d}} @ \lambda_{IR} = e^{-\alpha_A \Delta d} @ \lambda_{IR} \qquad (19)$$

Use of logarithms simplifies equation (19) to:

$$\ln(IR_L/IR_H) = \ln(e^{-\alpha_A \Delta d}) @ \lambda_{IR} = -\alpha_A \Delta d @ \lambda_{IR} \qquad (20)$$

The ratiometric combination of equations (16) and (20) yields:

$$\frac{\ln(R_L/R_H)}{\ln(IR_L/IR_H)} = \frac{-\alpha_A \Delta d @ \lambda_R}{-\alpha_A \Delta d @ \lambda_{IR}} \qquad (21)$$

Because the $\Delta d$ term in the numerator and denominator of the right-hand side of equation (21) cancel, as do the negative signs before each time, it will be appreciated that equation (21) when combined with equation (12) yields:

$$\text{Ratio} = R_{OS} = \frac{\alpha_A @ \lambda_R}{\alpha_A @ \lambda_{IR}} = \frac{\ln(R_L/R_H)}{\ln(IR_L/IR_H)} = \frac{\ln(R_H/R_L)}{\ln(IR_H/IR_L)} \quad (22)$$

Thus, by measuring the minimum and maximum emergent light intensities at both the red and infrared wavelengths ($R_L$, $R_H$, $IR_L$, $IR_H$), a value for the term $R_{OS}$ can be computed. From this, empirically derived calibration curves similar to that shown in FIG. 7 can be used to determine the oxygen saturation as described in greater detail in conjuction with the discussion of the various components of oximeter 10 that follows. As will be appreciated, the determination of oxygen saturation in this manner differs from prior art techniques, such as that disclosed by Wilber, by performing measurements based upon both the baseline and pulsatile components of the signals.

The first component of oximeter 10 to be discussed is sensor 12. The function of sensor 12 is substantially to provide the desired orientation of light sources 40 and 42, for example, light-emitting diodes (LEDs), and light detector 38 with respect to a suitable portion of a patient's body. For example, the sensor must align LEDs 40 and 42 with detector 38 in a manner such that the path of light from each LED to the detector 38 is substantially the same distance. In addition, the path must traverse a portion of the patient's body through which a usable amount of light is passed, for example, a finger, toe, earlobe, or the nasal septum. Because changes in the lightpath can significantly affect the readings taken, as noted above, the sensor must maintain the position of LEDs 40 and 42 and detector 38 with respect to the transmission path through the patient's skin at all times. Otherwise, signal fluctuations known as motion-artifact may be produced. In addition, the sensor should apply only insubstantial pressure to the patient's skin and underlying tissue. Otherwise, normal arterial blood flow upon which the pulse oximeter relies for accurate operation, may be disrupted. Finally, the sensor should be quickly attachable to the patient and should cause no discomfort.

Figure 11:
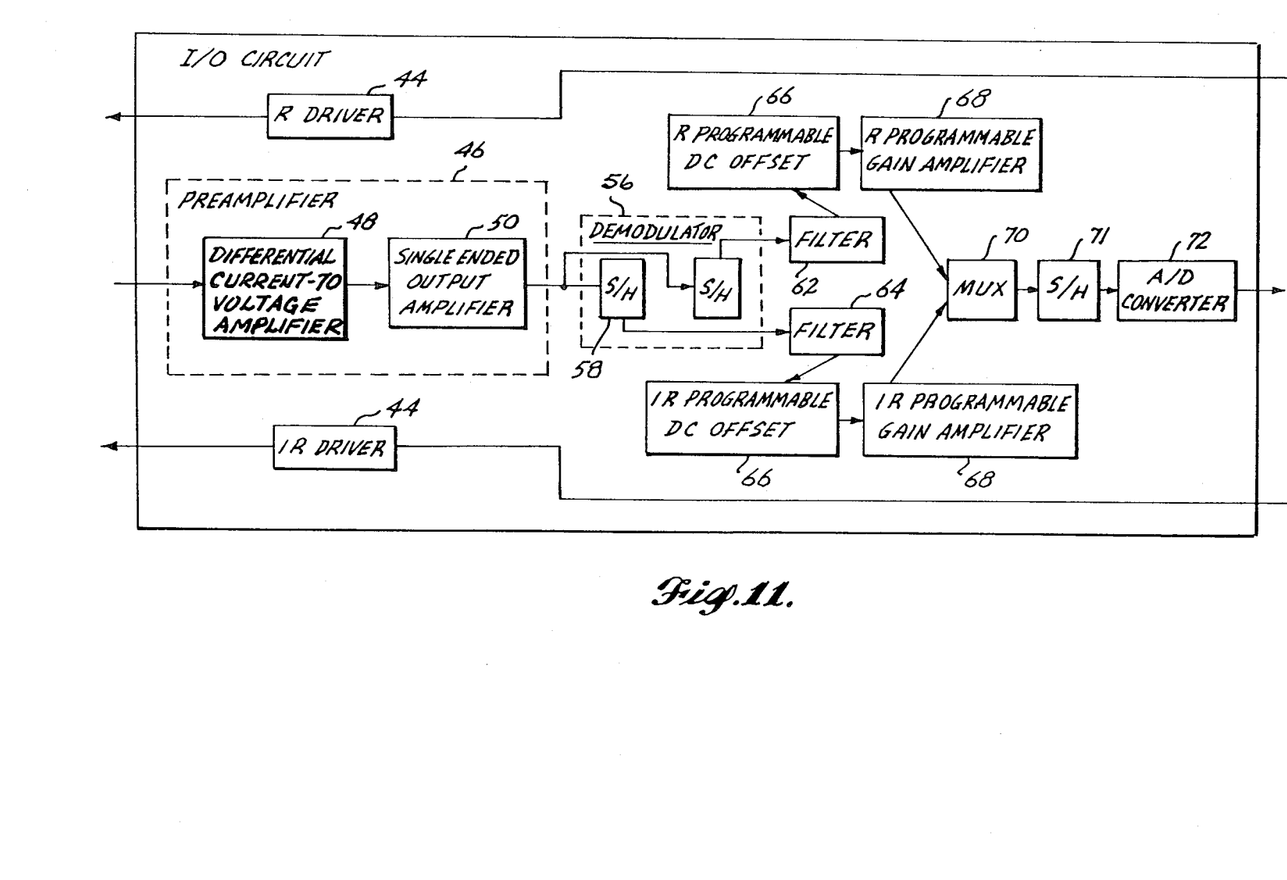
FIG. 11 is a more detailed schematic of the I/O circuit illustrated in the system of FIG. 1.

LEDs 40 and 42 are supplied with current by transistor drivers 44 located in the I/O circuit 14, as shown in FIG. 11. Drivers 44 are controlled by microcomputer 16 to produce current pulses at a 960 Hz repetition rate. The duration of each pulse is 70 microseconds and a pulse is supplied to the red wavelength LED 40 first and then to the infrared wavelength LED 42. The voltage drop across scaling resistors in the drivers 44 allows the magnitude of the current pulses to be determined and, thus, maintained in a manner described in greater detail below. LEDs 40 and 42 respond to the current pulses by producing corresponding light pulses transmitted through the finger to detector 38. Detector 38, in turn, produces a signal that includes information about the pulsatile response of the finger to the red and infrared wavelength light, intermixed at the 960 Hz LED pulse repetition rate.

In a preferred embodiment of the invention, a red optical filter 45 interrupts the lightpath between the LEDs 40 and 42 and the detector 38, as shown in FIG. 8. Preferably, filter 45 is a Kodak No. 29 wratten gel filter. Its function is to eliminate the influence of fluorescent light flicker on the oxygen saturation determination made. As will be appreciated, although the body of sensor 12 may be made of an opaque material that blocks a significant portion of the ambient light, some ambient light may still reach detector 38. Light from the sun and incandescent lamps is substantially continuous. Fluorescent lighting, on the other hand, includes alternating energized and deenergized intervals that form a visually imperceptible flicker. The frequency of the fluorescent light flicker is such that it might influence the signal produced by detector 38 in response to light received from LED 40 at the red wavelength. Thus, the red optical filter 45 is placed over the detector 38 and filters out any fluorescent light present, eliminating the effect its flicker might have on the oxygen saturation determination made.

Figure 12:
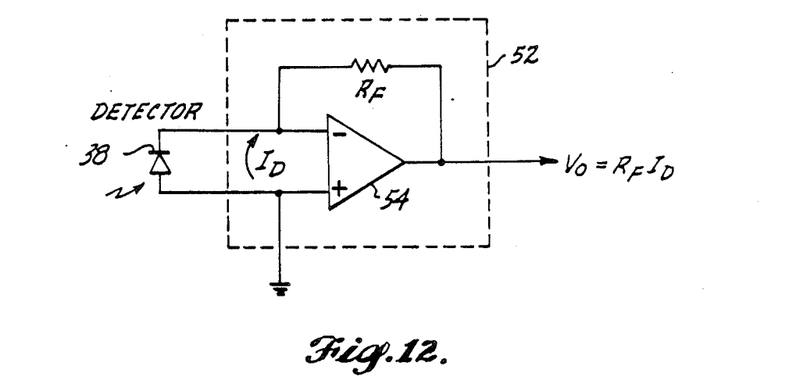
FIG. 12 is a schematic diagram of a conventional current-to-voltage amplifier circuit.

At the I/O circuit 14, the signal from detector 38 is received by a preamplifier 46. In a preferred embodiment, preamplifier 46 includes a differential current-to-voltage amplifier 48 and a single-ended output amplifier 50. To understand the advantages of using the differential amplifier 48, it may first be helpful to consider the operation of a conventional current-to-voltage amplifier as shown in FIG. 12. As shown, a current-to-voltage amplifier 52 is substantially comprised of an operational amplifier 54 and gain determination resistor $R_F$. With a detector 38 connected to the inputs of the amplifier as shown, a current $I_D$ is input to the amplifier upon the detection of suitable wavelength light. The output of amplifier 52 is designated $V_0$ and, as will be appreciated, is equal to the product of the detector current $I_D$ and the gain determination resistor $R_F$. The primary problem with such a construction is that it also amplifies the external interference noise produced, making the signal extracted less accurate.

Figure 13:
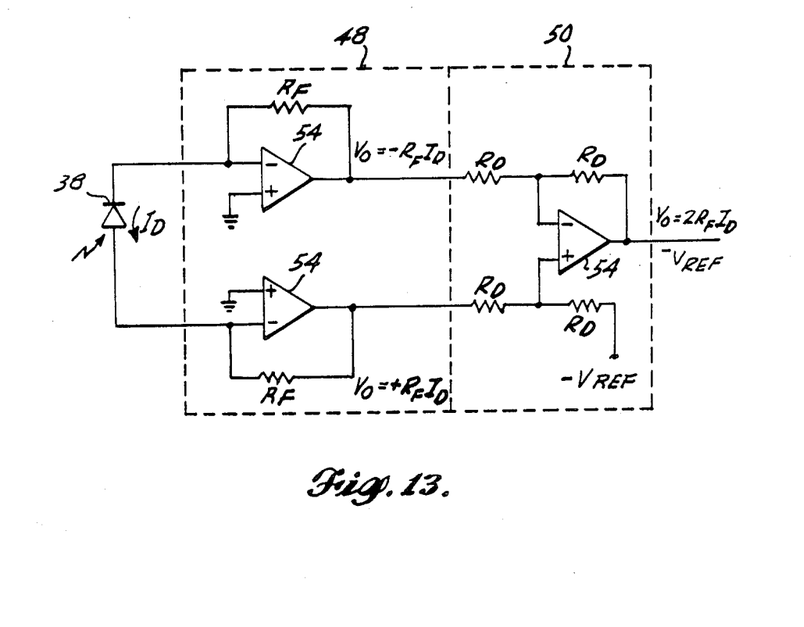
FIG. 13 is a schematic diagram of a differential, current-to-voltage preamplifier circuit included in the I/O circuit of FIG. 1.

Adoption of the differential current-to-voltage amplifier 48, when combined with the single-ended output amplifier 50 as shown in FIG. 13, however, eliminates this problem. As shown, the differential amplifier 48 produces positive and negative versions of the output, the absolute value of each version being equal to the product of the gain determination resistance $R_F$ and the detector current $I_D$. These outputs are then supplied to the single-ended output lamp 50, which provides unity gain, thus producing an output signal having a magnitude that is twice that of the inputs. An advantage of this arrangement is that external interference noise is cancelled at the single-ended output amplifier 50 by the opposing signs of the two transimpedance amplifier outputs. In addition, twice the signal is produced with the current noise only increasing by a magnitude of 1.414. Therefore, an improved signal-to-noise ratio results.

Figure 10:
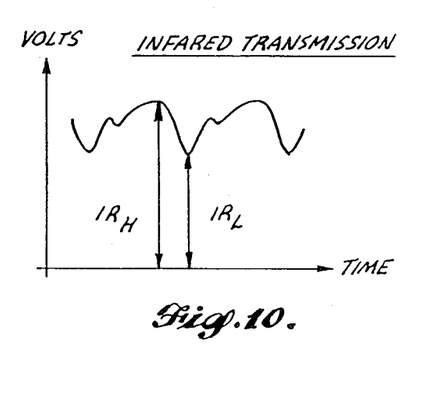
FIG. 10 is a graphical plot as a function of time of the transmission of infrared light through the finger.

At this point, the mixed signal indicative of the red and infrared wavelength responses of detector 38 has been amplified and is input to a demodulator 56 to extract the red pulsatile and infrared pulsatile waveforms shown in FIGS. 9 and 10. In a preferred arrangement, the demodulator 56 includes a sample-and-hold (S/H) circuit 60 that responds to the detector signal produced in response to red wavelength light and a sample-and-hold (S/H) circuit 58 that responds to the infrared wavelength response of detector 38. The timing of circuits 58 and 60 is controlled so that each circuit samples the signal input to demodulator 56 during the portion of the signal corresponding to the wavelength to which it responds. In this manner, two signals are reconstructed from the single input to demodulator 56. As noted above, these signals correspond to the red pulsatile signal and infrared pulsatile signals shown in FIGS. 9 and 10.

To remove high-frequency noise from the outputs of circuits 58 and 60, they are input to lowpass filters 62 and 64. In a preferred embodiment, the "red" lowpass filter 62 and "infrared" lowpass filter 64 each include two stages. The first stage of each filter utilizes a fifth-order monolithic integrated circuit switched capacitor filter because of its low cost, relatively small physical size and accuracy. Since both the "red" and "infrared" signals pass through nearly identical first-stage filters due to monolithic IC matching, their gain and phase frequency responses are matched. The second stage of each filter is a second-order Bessel filter having a slightly higher roll-off frequency than the first stage. This ensures that the first-stage filter is the dominant filter of the two-stage combination, producing the desired filtering accuracy. The second stage then filters the switching noise from the first-stage output.

The filtered red and infrared pulsatile signals are next prepared for conversion and transmission to the microcomputer 16. As will be discussed in greater detail below, this process involves the use of a programmable DC subtractor or offset 66 followed by a programmable gain amplifier 68 having a gain range from approximately one to 256. The appropriately processed signals are combined at multiplexer 70, sampled and held at 71, and converted to digital form by A/D converter 72 for transmission to microcomputer 16.

Before a more complete discussion of the operation of programmable subtractor 66, programmable gain amplifier 68, multiplexer 70, S/H 71, and A/D converter 72 is provided, several details regarding the signals to be transferred to microcomputer 16 should be noted. For example, as shown in FIGS. 9 and 10, the signal produced by detector 30 in response to light at each wavelength includes components that, for convenience, are termed baseline and pulsatile. The baseline component approximates the intensity of light received at detector 38 when only the "fixed" nonpulsatile absorptive component is present in the finger. This component of the signal is relatively constant over short intervals but does vary with nonpulsatile physiological changes or system changes, such as movement of sensor 12 on the finger. Over a relatively long interval this baseline component may vary significantly. As will be appreciated, the magnitude of the baseline component at a given point in time is substantially equal to the level identified in FIG. 9 as $R_H$. For convenience, however, the baseline component may be thought of as the level indicated by $R_L$, with the pulsatile component varying between the values for $R_H$ and $R_L$ over a given pulse. That pulsatile component is attributable to light transmission changes through the finger resulting from blood volume changes in the finger during a cardiac pulse. Typically, the pulsatile component may be relatively small in comparison to the baseline component and is shown out of proportion in FIGS. 9 and 10.

The determination of $R_{OS}$ in accordance with equation (22) requires accurately measured values for both the baseline and pulsatile signal components. Because the pulsatile components are smaller, however, greater care must be exercised with respect to the measurement of these components. As will be readily appreciated, if the entire signal shown in FIGS. 9 and 10, including the baseline and pulsatile components, was amplified and converted to a digital format for use by microcomputer 16, a great deal of the accuracy of the conversion would be wasted because a substantial portion of the resolution would be used to measure the baseline component. For example, with an A/D converter employed having an input range of between +10 and −10 volts, a signal having a baseline component referenced to −10 volts that is four times that of the pulsatile component can be amplified until the baseline component is represented by a 16-volt difference and the pulsatile signal represented by a 4-volt difference. With a 12-bit A/D converter 72, the total signal can be resolved into 4096 components. Therefore, the number of incremental levels representing the pulsatile signal would be approximately 819. If, on the other hand, the baseline component is removed prior to the conversion, the gained pulsatile signal could be resolved into 4096 intervals, substantially improving accuracy.

Figure 14:
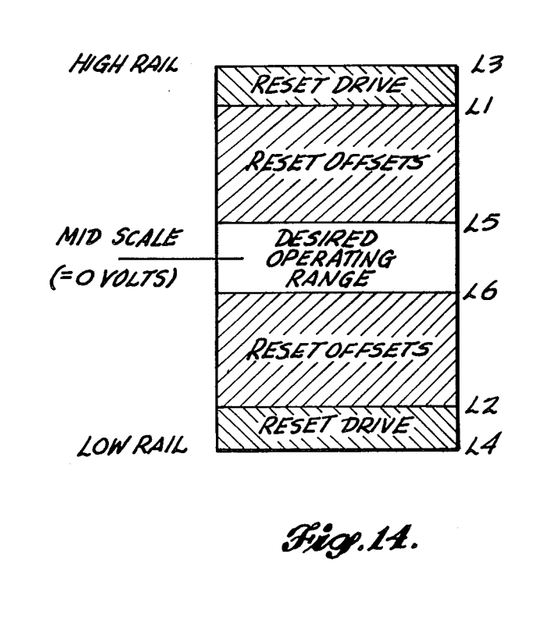
FIG. 14 is a graphical representation of the possible ranges of I/O circuit output, showing the desired response of the I/O circuit and microcomputer at each of the various possible ranges.

The disclosed invention employs this technique, as the first half of a construction-reconstruction process, in the manner schematically outlined in FIG. 14. As shown, an input signal $V_1$ (corresponding to the signals shown in FIGS. 9 and 10) is received from each filter 62 and 64. $V_1$ includes both the baseline and pulsatile components discussed above. As will be described, subsequent operations upon $V_1$ subtract off a substantial "offset voltage" portion of the baseline component, then gain up the remaining substantially pulsatile signal for conversion by A/D converter 72. A digital reconstruction of the original signal is then produced by reversing the process, wherein digitally provided information allows the gain to be removed and the offset voltage added back. This step is necessary because the entire signal, including both the baseline and pulsatile components, is used in the oxygen saturation measurement process.

Feedback from microcomputer 16 to I/O circuit 14 is also required to maintain the values for the offset voltage, gain, and driver current at levels appropriate to produce optimal A/D converter 72 resolution. Proper control requires that the microcomputer continually analyze, and respond to, the offset voltage, gain, driver currents and the output of A/D converter 72 in a manner to be described next.

Briefly, with reference to FIG. 15, thresholds L1 and L2 slightly below and above the maximum positive and negative excursions L3 and L4 allowable for the A/D converter 72 input are established and monitored by microcomputer 16 at the A/D converter 72 output. When the magnitude of the signal input to, and output from, A/D converter 72 exceeds either of the thresholds L1 or L2, the driver currents $I_D$ are readjusted to decrease the intensity of light impinging upon the detector 38. In this manner, the A/D converter 72 is not overdriven and the margin between L1 and L3 and between L2 and L4 helps assure this even for rapidly varying signals. An operable voltage margin for A/D converter 72 exists outside of the thresholds, allowing A/D converter 72 to continue operating while the appropriate feedback adjustments to A and $V_{OS}$ are made.

When the signal from A/D converter 72 exceeds positive and negative thresholds L5 or L6, microcomputer 16 responds by signaling the programmable subtractor 66 to increase the offset voltage being subtracted. This is done through the formation and transmission of an offset code whose magnitude is dependent upon the level of the signal received from converter 72.

Figure 15:
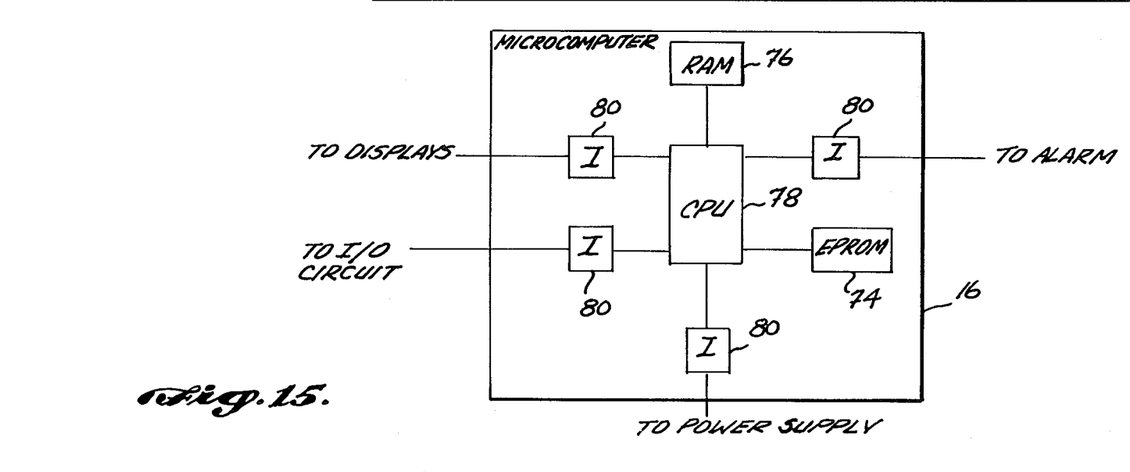
FIG. 15 is a more complete schematic diagram of the microcomputer illustrated in FIG. 1.

Three different gain adjustments are employed in the arrangement graphically depicted in FIG. 15. For example, if microcomputer 16 determines that the A/D converter 72 signal has not exceeded positive and negative thresholds L7 and L8, the current value of a gain code is increased. This revised gain code is then transmitted to the programmable amplifier 68, which makes the appropriate adjustment to the signal A. If the A/D converter signal exceeds positive and negative thresholds L9 and L10, the gain code is adjusted downward as a function of the signal magnitude. Similarly, if separate lower positive and negative thresholds L11 and L12 are exceeded, the gain code is also adjusted downward as a separate function of the signal magnitude.

The manner in which the various thresholds are established and the relationship of the gain and offset codes to the signal received can be altered to produce substantially any form of control desired. Thus, the arrangement shown in FIG. 15 is illustrative only and represents the currently preferred embodiment.

Figure 16:
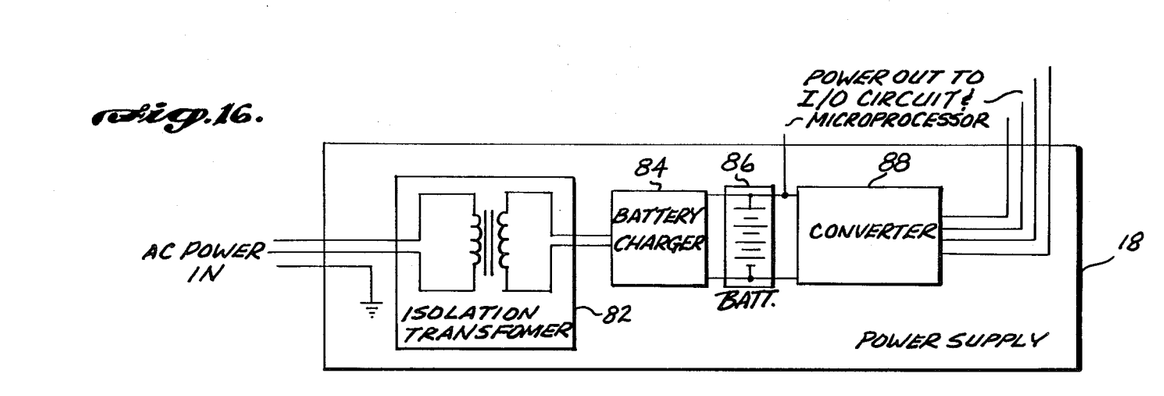
FIG. 16 is a more complete schematic diagram of the power source illustrated in FIG. 1.

As will be appreciated from FIG. 16, the instructions for the microcomputer program that controls the signal construction-reconstruction discussed above are stored in erasable, programmable, read-ony memory (EPROM) 74 of microcomputer 16. Similarly, values for $R_H$, $IR_H$, $R_L$, $IR_L$, and signal period (pulse duration) are determined pursuant to peak-detection software contained in EPROM 74. These values are stored in random-access memory (RAM) 76 for operation upon by a central processing unit (CPU) 78 in accordance with further computational instructions stored in EPROM 74. Interfaces 80 act as input and output buffers for microcomputer 16.

The computational software in EPROM 74 allows CPU 78 to determine both oxygen saturation and pulse rate. Initially the program directs CPU 78 to determine the present value for $R_{OS}$ by substituting the measured values for $R_H$, $IR_H$, $R_L$, and $IR_L$ into equation (22):

$$R_{OS} = \frac{\ln(R_L/R_H)}{\ln(IR_L/IR_H)} \quad (22)$$

Then, the computational software instructs CPU 78 to determine the oxygen saturation from $R_{OS}$ by use of a calibration curve such as the one depicted in FIG. 7. The calibration curve is a plot of the relationship between independently determined oxygen saturations corresponding to values of $R_{OS}$ produced by oximeter 10 in accordance with the technique described above.

With sufficiently large space in EPROM 74, enough points along the calibration curve can be stored in a look-up table to allow CPU 78 to extract an accurate indication of oxygen saturation from the value of $R_{OS}$ input to EPROM 74. The storage of a sufficient number of calibration curve data points may, however, necessitate the use of an undesirably large capacity EPROM 74. For that reason, a second method of storing the calibration curve information is preferred.

Pursuant to that method, once independently derived data associating $R_{OS}$ with the oxygen saturation is obtained, a mathematical expression between the two can be derived from a plot of the curve. The basic formula and the coefficients of the formula's variables are then stored in EPROM 74. When a value for $R_{OS}$ is measured, CPU 78 extracts the coefficients from EPROM 74 and computes a value for the oxygen saturation. This technique allows information completely identifying the entire calibration curve, or a family of such curves, to be stored within a relatively small amount of EPROM 74 space.

Before discussing the manner in which information extracted by oximeter 10, as outlined above, is made available to an operator, a brief description of power source 18 is provided. As shown in FIG. 16, grounded AC power is input to power source 18 from, for example, a wall outlet. An isolation transformer 82 is employed between the AC supply and a battery charger 84. The battery charger 84 allows battery 86 to charge whenever the oximeter 10 is plugged into a wall outlet. Battery 94 is constructed to operate oximeter 10 for approximately one hour in the absence of AC power input. A converter 88 conditions the output of battery 86 to provide the various DC supply voltages required by the I/O circuit 14 and microcomputer 16 to produce the various information to be displayed.

The output of information produced by oximeter 10 is now discussed in greater detail with reference to FIG. 17, which illustrates the front panel of an oximeter constructed in accordance with this invention. As shown, a panel 90 supports user input keyboard 22, as well as the various displays 20.

Keyboard 22 includes a POWER switch 92, which, for example, may be a momentary, tactile membrane switch. When switch 92 is depressed, oximeter 10 is activated. The oximeter 10 will operate off AC power when it is available; otherwise, DC power from battery 86 is used. The battery charger 84 will charge battery 86 as long as oximeter 10 is plugged in, and is not dependent on the operation of POWER switch 92.

A SELECT switch 100 is used to sequence through the various operational limits of oximeter 10, allowing them to be adjusted, as described in greater detail below. The particular limit selected can be identified by, for example, the flashing of a predetermined portion or the entirety of a corresponding display on panel 90. Momentary depression of switch 100 causes an incremental progression through a predetermined order of the limits, while continued depression provides automatic stepping through the various limits. When switch 100 has not been depressed for a predetermined amount of time, microcomputer 16 indicates that none of the limits are to be adjusted and returns oximeter 10 to normal operation. The SELECT switch 100 progresses through the various operating limits in a predetermined sequence, preferably beginning with an initial, normal operating mode. In this mode, none of the operating limits of oximeter 10 can be adjusted.

RAISE and LOWER switches 102 and 104 (indicated on keyboard 22 by upwardly and downwardly directed triangles) are used in conjunction with LIMIT SELECT switch 100 in the following manner. With switch 100 used to select the particular limit to be adjusted, the level of the limit can be raised by depressing switch 102 and lowered by depressing switch 104. Once adjusted, a particular limit is set by another depression of switch 100. Similar to the operation of LIMIT SELECT switch 100, momentary depression of the RAISE and LOWER switches 102 and 104 produces an incremental adjustment in the operating limit while continuous depression produces continuous change. The operating limit may include an "OFF" position at the upper limit of adjustment reached by depressing the RAISE switch 102 as well as an "OFF" position at the lower limit of adjustment reached by depressing LOWER switch 104.

The visual display of the basic oxygen saturation and pulse rate produced by oximeter 10, are achieved by displays 20. As shown in FIG. 17, these displays include a vertical column of light-emitting diodes (LEDs) and a plurality of digital LED displays.

Figure 17:
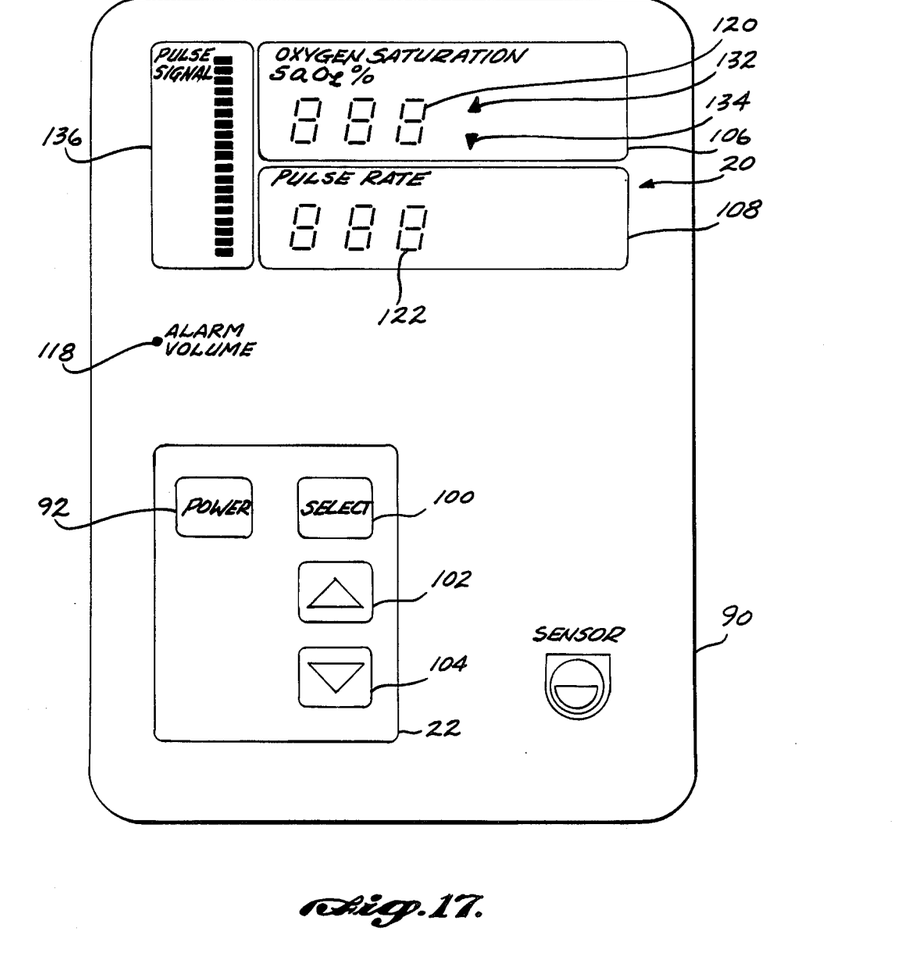
FIG. 17 is a detailed view of the front panel of an oximeter constructed in accordance with the present invention illustrating some of the displays employed.

Addressing now the digital display elements of display panel 20, as shown in FIG. 17, the oxygen saturation display 106 includes a three-digit display 120 that indicates the oxygen saturation currently determined by microcomputer 16. As will be appreciated, three-digit display 120 allows oxygen saturation to be expressed in one-percent increments over the entire range of oxygen saturations to be encountered. The pulse display 108 also includes a three-digit display 122 of the pulse rate currently measured by oximeter 10. This dispay allows the pulse to be expressed in, for example, one-beat-per-minute increments over the entire range of pulse rates to be encountered. Displays 120 and 122 are substantially the same size.

The displays included on panel 90 that are of particular interest are the oxygen saturation trend displays 132 and 134 and the pulse perfusion bar display 136. In a preferred embodiment, trend display 132 is an upwardly directed, triangular LED display, which indicates that the oxygen saturation monitored by oximeter 10 has increased at a rate in excess of some predetermined minimum. Similarly, trend display 134 is a downwardly directed, triangluar LED display, which indicates that the oxygen saturation has decreased at a rate in excess of some predetermined minimum. As will be appreciated, displays 132 and 134 provide the operator of oximeter 10 with qualitative information about oxygen saturation activity in the patient that may be inconvenient to obtain from display 120. For example, unless a physical or mental record of the oxygen saturation indicated at display 120 is kept, a physician may be unable to quickly determine whether the oxygen saturation has been progressively drifting in a particular direction. In some instances, this change in oxygen saturation may presage the occurrence of potentially harmful physiological changes, even before the upper and lower oxygen saturation alarm limits have been reached. Displays 132 and 134 provide the operator with this information in a convenient, easily read manner.

The manner in which such qualitative displays are controlled by microcomputer 16 is as follows. CPU 78 stores the value of the oxygen saturation output by display 120 in RAM 76 at a first time and at a second tine, some predetermined time later. The interval between these first and second measurement times may be of fixed duration, for example, two minutes, or a function of the pulse, for example 150 beats. CPU 78 then compares the oxygen saturation stored at the two times and, if the change in oxygen saturation is greater than, for example, three percent, and the sign of the current slope corresponds to the sign of the slope over the specified interval, the appropriate trend indication display is lit. Once lit, displays 132 and 134 remain on until the rate at which the oxygen saturation changes drops below a second predetermined level, for example, a 2.5 percent full-scale change over a two-minute interval or the sign of the current slope of the oxygen saturation no longer corresponds to the direction of the lit trend indicator display. CPU 78 repeats this test at intervals that may be of fixed duration or a function of pulse. Thus, the change in oxygen saturation may be redetermined, for example, every five seconds or every five pulses.

Figure 18:
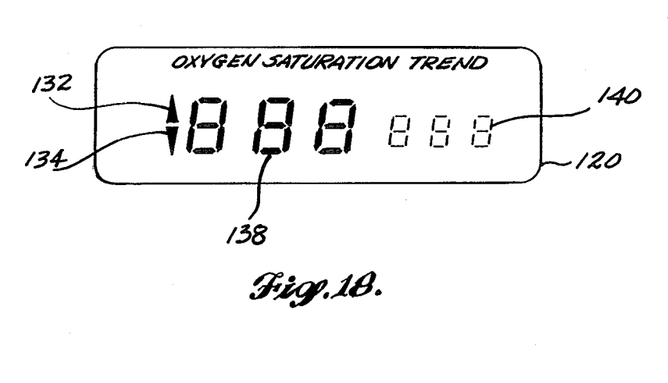
FIG. 18 is an alternative display for use on the front panel shown in FIG. 17 to indicate oxygen saturation trends.

As will be appreciated, the oxygen saturation trend indication displays outlined above can be alternatively implemented and supplemented in a variey of fashions. For example, as shown in FIG. 18, a display 120 for inclusion on panel 90 also includes a digital oxygen saturation trend display 138 and a trend-rate adjustment display 140. In this arrangement, CPU 78 continually updates oxygen saturation information in RAM 76 and then processes it to determine whether it has been increasing or decreasing at a rate in excess of the rates stored in RAM 76 in the following manner.

LIMIT SELECT switch 100 is used to access second and third operating limit adjustment modes. These modes allow adjustment of the rates that must be exceeded to light triangular trend displaye 132 and 134, respectively. For example, with LIMIT SELECT switch 100 depressed until the second mode is reached, triangular LED 132 and adjustment display 140 are both flashed continuously. Then, with the aid of RAISE and LOWER switches 102 and 104, the rate above which the oxygen saturation must increase to light display 132 can be increased or decreased. When the proper rate has been set, LIMIT SELECT switch 100 is again depressed and the new rate stored in RAM 76.

In a similar manner, the rate above which oxygen saturation must decrease to light display 134 can be adjusted when the third mode has been selected by LIMIT SELECT switch 100. In this case, trend display 134 and trend adjustment display 140 flash and the threshold rate is adjusted by RAISE and LOWER switches 102 and 104. Although not depicted in FIG. 18, it will be appreciated that a second trend-rate adjustment display can be employed in conjunction with display 140 to allow the rates of oxygen saturation change necessary to extinguish LEDs 132 and 134 to be adjusted. These rates, however, may be a fixed percentage of the rates set above.

An alarm produced by a speaker can be employed to simultaneously sound with the lighting of displays 132 and 134. The volume of the audible alarm is adjusted by repeatedly operating LIMIT SELECT switch 100 until a "set alarm volume" mode is reached. Then RAISE and LOWER switches 102 and 104 are used to raise and lower the alarm volume. The alarm volume, as set, determines the volume of the audible tone produced by the speaker when the oxygen saturation has changed sufficiently to light LEDs 132 and 134. An ALARM VOLUME indicator 118 indicates that the alarm volume adjustment mode in the alarm limit sequence 118 activated by LIMIT SELECT switch 100 has been reached. Thus, light 118 notifies the operator that the alarm volume can now be raised or lowered by use of RAISE and LOWER switches 102 and 104.

The other display shown in FIG. 17 to be particularly noted is the pulse/perfusion bar display 136. In the arrangement shown, bar display 136 includes a plurality of vertically aligned individual LEDs 142. For example, a display 136 comprised of 20 LEDs 142 has been found to provide acceptable resolution. As will be described in greater detail below, bar display 136 provides a visual indication of pulse signal quality, pulse level, and perfusion over a broad range of perfusions. Signal quality basically is an indication of the influence of noise on the signal received. The signal level is a measure of the signal level relative to that required by the oximeter to operate properly. Perfusion indicates the relative volume of the arterial blood flowing in the tissue. These various parameters are combined in a useful manner by bar display 136.

As will be appreciated from the basic discussion of oximetry theory and oximeter 10 provided above, the pulse rate can be extracted from the signals input to microcomputer 16 by use of peak detection program stored in EPROM 74. In addition, because the intensity of light impinging upon detector 38 is a function of the blood volume in the tissue analyzed, the signal received by microcomputer 16 from I/O circuit 14 can be used to indicate the perfusion. This information is provided on display 136 as a "filled" bar with the origin at the bottom of the display. Thus, an increasing number of LEDs 142 will be lit as arterial blood volume in the tissue approaches a maximum and they will be progressively extinguished as the blood volume returns to a minimum. Taken as a whole, display 136 will appear to rise and fall once for the occurrence of each pulse.

In operation, any signal greater than a predetermined minimum threshold is automatically scaled to the level necessary to light all of the individual LEDs 142 when maximum blood volume is present. As noted previously, the peak detection software in EPROM 74 allows the peaks of the signal input to microcomputer 16 to be determined and it is these peaks that are autoscaled by CPU 78 in accordance with further EPROM 74 instructions to produce full-scale deflection on display 136. While a linear display could be employed in conjunction with the automatic scaling described above, certain advantages may be produced by representing the varying indication of perfusion derived from display 136 between the full-scale occurrences of each pulse as a logarithmic function of the perfusion. Thus, for example, a tenfold drop in blood volume between maximum and minimum blood volumes would only produce a half-scale drop in display 136. As will be appreciated, use of such logarithmic scaling provides greater resolution for small changes near full-scale deflection but renders display 136 substantially unresponsive to similar changes well below full-scale. In this manner, the attenuation in the signal produced by the pulsatile component, which, after all, is the part that indicates blood volume, is emphasized in display 136 and the portion of the attenuation attributable to the fixed components is substantially ignored.

When the minimum threshold required for automatic scaling of the signal to produce peak deflection of display 136 has not been reached, the incoming signal amplitude may be either linearly or logarithmically scaled on display 136. Use of logarithmic scaling retains the advantages of improved resolution discussed above even when the perfusion of the patient being monitored is relatively low. If the peak amplitude produced by the signal on display 136 falls below a predetermined threshold (e.g., 1/20 full-scale deflection), one LED is lit and is stepped up the pulse bar until an acceptable pulse is locked onto again.

While the invention has been described with reference to a preferred embodiment, it is to be clearly understood by those skilled in the art that the invention is not limited thereto, and that the scope of the invention is to be interpreted only in conjunction with the following claims.

The embodiments of the invention in which an exclusive property or privilege is claimed are defined as follows:

1. An apparatus, for processing signals containing information about the oxygen saturation of arterial blood flowing in tissue, comprising:
   processing means for determining the oxygen saturation of said arterial blood flowing in said tissue from said signals; and
   display means for producing a numeric representation of the change in said oxygen saturation during a specified interval.

2. The apparatus of claim 1, further comprising first and second trend indication displays, said first trend indication display producing an output when said oxygen saturation has increased by a first predetermined amount during said specified interval, said second trend indication display producing an output when said oxygen saturation has decreased by a second predetermined amount during said specified interval.

3. A method of processing signals containing information about the oxygen saturation of arterial blood flowing in tissue comprising the steps of:
   producing an indication of the oxygen saturation of said arterial blood flowing in said tissue from said signals; and
   producing a numeric representation of the change in said oxygen saturation during a specified interval.

4. The method of claim 3, wherein said step of displaying said output further comprises the steps of producing a first display when said oxygen saturation has increased by a first predetermined amount during said specified interval and producing a second display when said oxygen saturation is decreased by a second predetermined amount during said specified interval.

* * * * *